United States Patent [19]

Wolff

[11] Patent Number: 4,871,657
[45] Date of Patent: Oct. 3, 1989

[54] COLOR PHOTOGRAPHIC RECORDING MATERIAL WITH EASILY DISPERSIBLE COLOR COUPLERS

[75] Inventor: Erich Wolff, Solingen, Fed. Rep. of Germany

[73] Assignee: Agfa-Gevaert Aktiengesellschaft, Leverkusen, Fed. Rep. of Germany

[21] Appl. No.: 317,109

[22] Filed: Feb. 28, 1989

Related U.S. Application Data

[63] Continuation of Ser. No. 909,630, Sep. 22, 1986, abandoned.

[30] Foreign Application Priority Data

Oct. 3, 1985 [DE] Fed. Rep. of Germany ....... 3535247

[51] Int. Cl.⁴ ................................................ G03C 7/32
[52] U.S. Cl. ..................................... 430/548; 430/552; 430/553; 430/554; 430/555; 430/556; 430/557; 430/558
[58] Field of Search ............... 430/546, 551, 552, 553, 430/554, 555, 556, 557, 558, 548

[56] References Cited

U.S. PATENT DOCUMENTS 4,513,082 4/1985 Furutachi et al. ................... 430/554
4,666,825 5/1987 Shimba et al. ....................... 430/552

FOREIGN PATENT DOCUMENTS 0108845 6/1985 Japan .................................... 430/553

Primary Examiner—Paul R. Michl
Assistant Examiner—Lee C. Wright
Attorney, Agent, or Firm—Connolly and Hutz

[57] ABSTRACT

A color photographic recording material having at least one silver halide emulsion layer contains at least one coupler corresponding to the general formula I

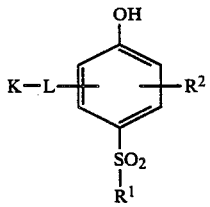

wherein
  K represents a coupler group,
  L a direct bond of a linking member,
  $R^1$ alkyl, aralkyl, aryl or amino and
  $R^2$ hydrogen or a group -L-K.

The couplers of formula I are suitable for high temperature processing without the presence of benzyl alcohol.

1 Claim, No Drawings

COLOR PHOTOGRAPHIC RECORDING MATERIAL WITH EASILY DISPERSIBLE COLOR COUPLERS

This application is a continuation, of application Ser. No. 909,630, filed Sept. 22, 1986 now abandoned.

This invention relates to a colour photographic recording material having at least one silver halide emulsion layer and containing couplers which have excellent solubility in organic solvents due to the presence of special substituents.

It is known to produce colour photographic images by chromogenic development, i.e. by developing image-wise exposed silver halide emulsion layers by means of suitable colour forming developer substances, so-called colour developers, in the presence of suitable colour couplers so that the oxidation product of developer substances formed in correspondence with the silver image reacts with the colour coupler to form a dye image. The colour developers used are normally aromatic compounds containing primary amino groups, in particular those of the p-phenylenediamine series.

The colour couplers and the dyes obtained from them by chromogenic development are required to satisfy numerous conditions. Firstly, the colour couplers should have as high as possible a coupling velocity with the oxidation product of the colour developer. Furthermore, the colour couplers and the dyes obtained from them should be sufficiently stable to light, elevated temperatures and moisture. This applies both to the freshly prepared recording materials and to the processed materials. For example, the residual coupler present in the image whites of the processed material must not undergo yellowing. In addition, the dyes should be sufficiently stable in the presence of gaseous reducing or oxidizing agents, and they must be fixed in a diffusion-fast form in the image layer and should be deposited as a very fine grain in the course of chromogenic development. The colour couplers must not impair the mechanical properties of the layers and the dyes formed from the colour couplers as a result of chromogenic development should have a suitable absorption curve with a maximum corresponding to the colour of the desired partial image and be as far as possible free from side absorptions. Thus in the ideal case a magenta dye, for example, should absorb green light almost completely and be substantially transmittent to both blue and red light.

Furthermore, the colour couplers should be highly soluble in organic solvents so that stable dispersions can be prepared from them in hydrophilic media, in particular in the binders used in photographic recording materials. The couplers should not agglomerate or crystallise from such dispersions nor from the freshly prepared colour photographic materials as this would result in a loss of sensitivity and colour yield. Lastly, the couplers should be insensitive or relatively insensitive to variations in operating conditions, in particular variations in temperature, pH or composition of the processing baths.

Another important requirement arises from the fact that modern colour photographic recording materials are increasingly being processed at higher temperatures. As the higher temperatures result in shorter development times, they frequently require the use of solubilizing additives in the processing baths to enable sufficient colour densities to be achieved. The solubilizing additives used may be, for example, hydrophilic organic solvents such as benzyl alcohol, which is a conventional constituent of colour photographic developer baths. The use of such additives gives rise to additional problems which are at least partly due to the fact that the colour photographic recording material to be processed carries these additives from one treatment bath (e.g. developer) to the next (e.g. bleach fixing bath) so that the first mentioned bath is depleted of additive and the next bath becomes more concentrated. Constant monitoring and replenishment of the baths is therefore necessary in order that constant results may be obtained. Furthermore, elaborate precautions are necessary to prevent these additives getting into the effluent where they would have the undesirable effect of permanently increasing the chemical and biological oxygen requirement. It is therefore very desirable to avoid the use of such solubilizing additives as far as possible.

Couplers with special ballast groups capable of producing advantageous results with respect to the above-mentioned aims have already been described in EP-A-0 073 636, US-A-4 503 141 and US-A-4 513 082. The couplers described are, however, not satisfactory in every respect and there is therefore still a need for couplers providing a further improvement in properties.

It is an object of the present invention to provide a colour photographic recording material containing colour couplers which have excellent solubility in organic solvents and are therefore easily incorporated in the layers of colour photographic recording material. The recording material should be suitable for high temperature processing and capable of giving rise to image dyes with high colour density even in the absence of solubilizing organic additives such as benzyl alcohol.

The present invention relates to a colour photographic recording material having at least one silver halide emulsion layer and at least one coupler containing a phenyl group substituted with a hydroxyl group and a sulphonyl group, characterised in that the coupler corresponds to the following general formula I

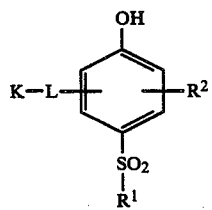

wherein
K represents a coupler group,
L represents a direct bond or a linking member,
$R^1$ represents alkyl, aralkyl, aryl or amino and
$R^2$ represents hydrogen or a group -L-K.

The coupler group represented in formula I contains a coupling function, i.e. a group which is capable of coupling with the oxidation product of a colour developer under the conditions of photographic development. The coupler group K represents the residue of a coupler, e.g. the residue of a yellow coupler of the type of α-acylacetanilide, a magenta coupler of the type of 3-anilino- or 3-acylamino-1-arylpyrazolone or of pyrazolotriazole, or a phenolic or naphtholic cyan coupler. The couplers according to the invention may be 2- or 4-equivalent couplers, i.e. the coupling position may be either unsubstituted or substituted with a group capable of being released in the process of development. These releasable groups may be, for example, halogen atoms or organic groups attached to the coupling position by an oxygen, sulphur or nitrogen atom. These groups are in many cases residues of heterocyclic compounds attached to the coupling position by a ring nitrogen atom.

The phenyl group substituted by a hydroxyl group and a sulphonyl represented in formula I may also be such a releasable group and may be attached to the coupling position of the coupler by a linking member although it is generally attached to the coupler group K by way of a non-coupling position.

The alkyl group represented by $R^1$ in formula I is an alkyl group with 1 to 4 carbon atoms, preferably methyl or ethyl.

The aryl group represented by $R^1$ in formula I is preferably phenyl, either unsubstituted or substituted, e.g. by alkoxy such as methoxy or hexadecyloxy, benzyloxy or phenoxy.

An amino group in formula I is preferably a secondary amino group such as a dialkylamino group (dimethylamino, diethylamino) or a cyclic amino group such as piperidino, purrolidino or morpholino.

Preferred couplers according to the invention may be represented by the following general formula II:

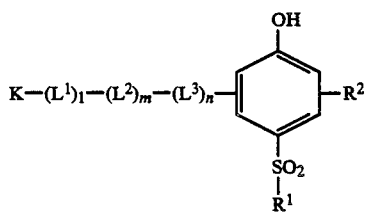

II wherein K, $R^1$ and $R^2$ have the meanings already indicated and l, m and n represent, independently of one another, 0 or 1;

$L^1$ represents —NH— or

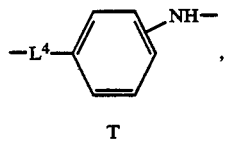

$L^2$ represents —CO—, —CO—CH$_2$—CH$_2$—CO—,

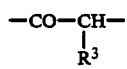

or $R^4$, $L^3$ represents O, NH or NH—$L^5$,
$L^4$ represents O, S, $NR^5$ or $R^6$,
$L^5$ represents $R^7$ or

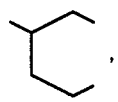

T represents hydrogen, halogen or alkoxy,
$R^3$ and $R^5$ represents hydrogen or an alkyl group having 1 to 20 carbon atoms, and
$R^4$, $R^6$ and $R^7$ represent alkylene with 2 to 4 carbon atoms.

Some couplers according to the invention are shown below by way of example.

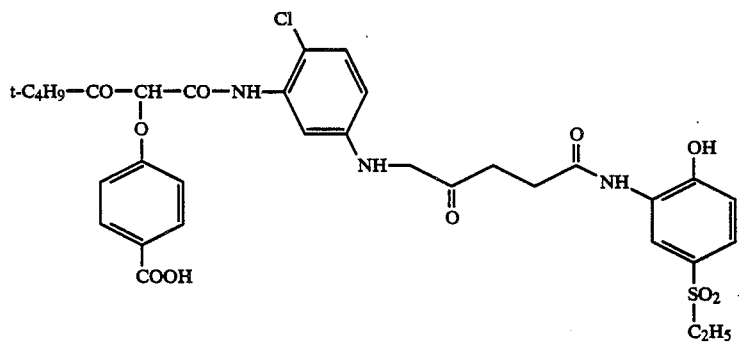

Y-1

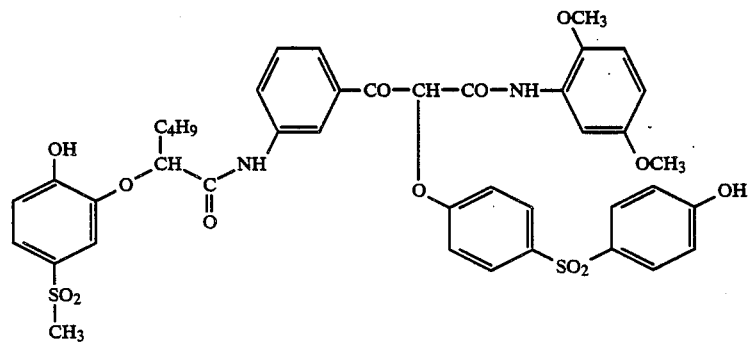

Y-2

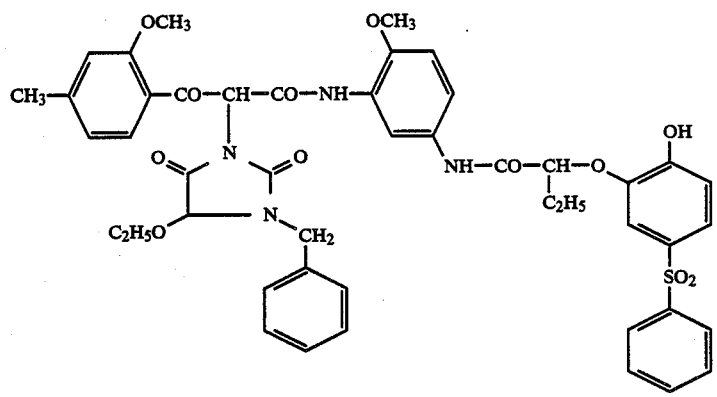
Y-3
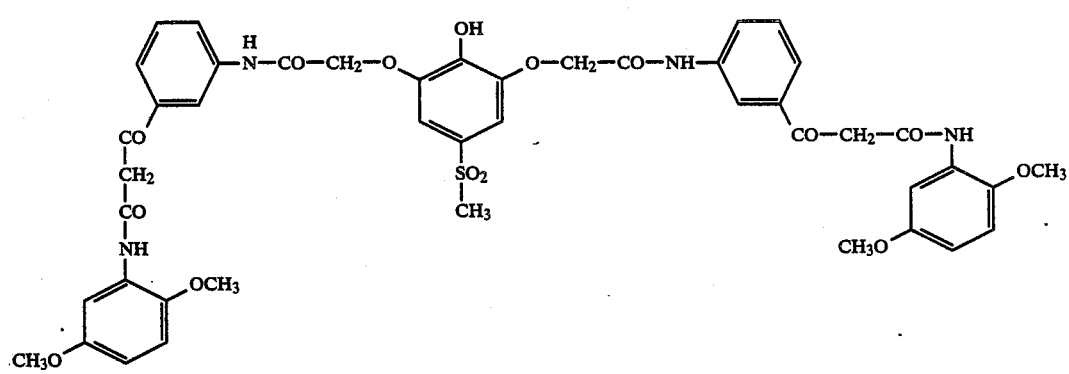
Y-4
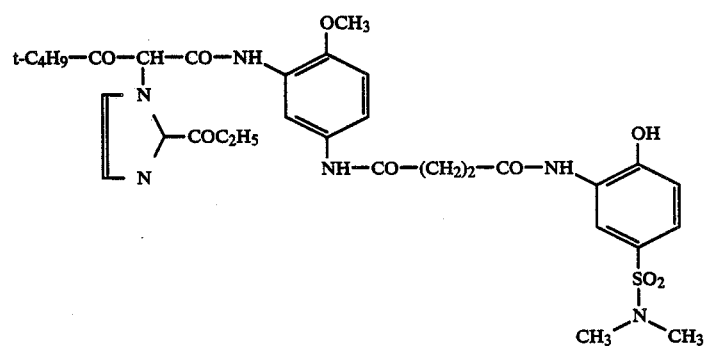
Y-5
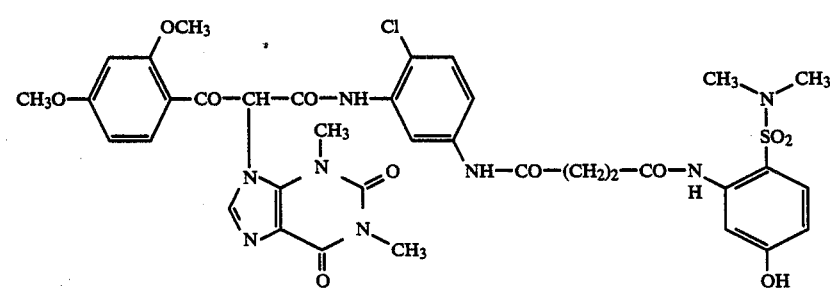
Y-6

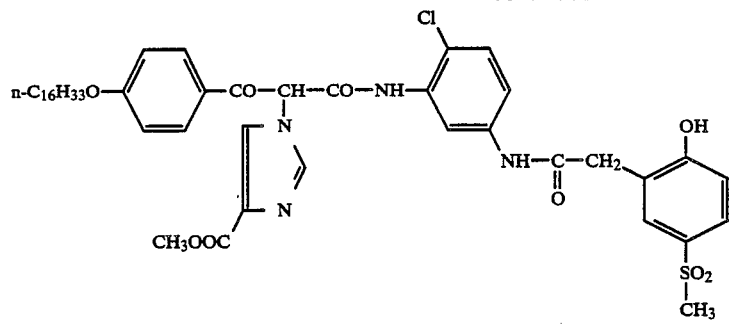
Y-7
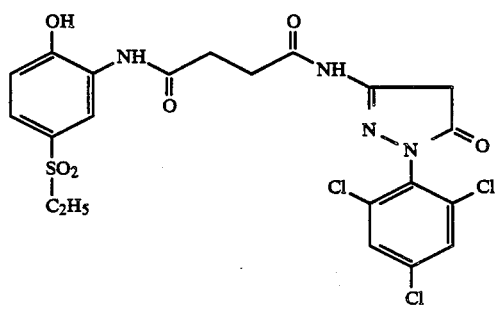
M-1
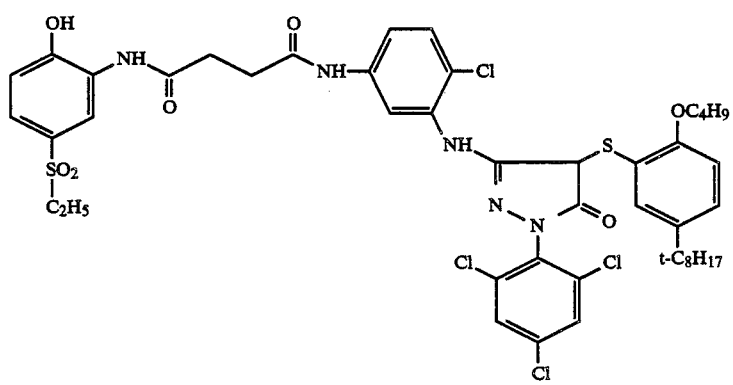
M-2
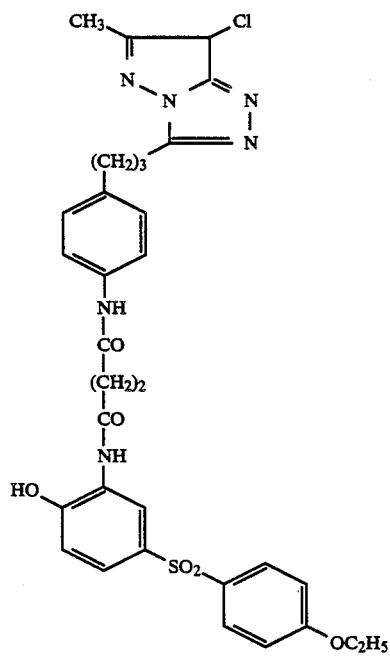
M-3

-continued
M-4
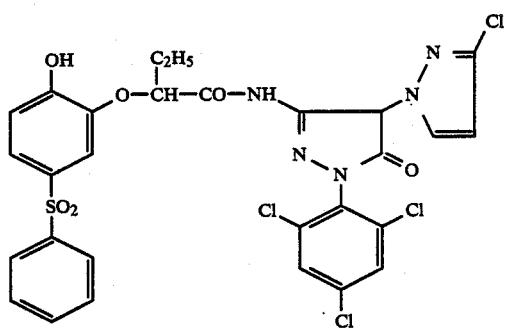
M-5
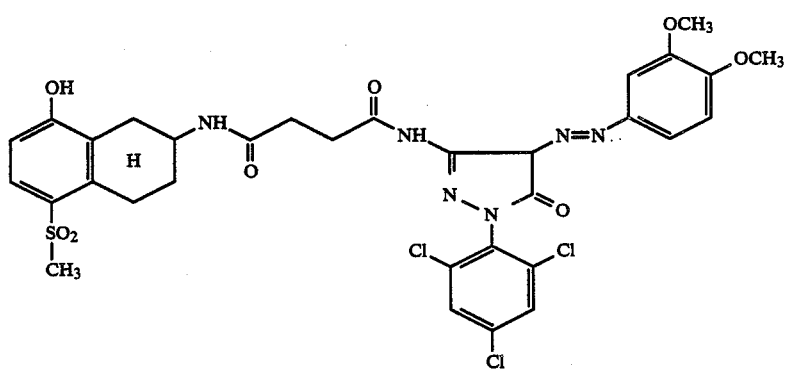
M-6
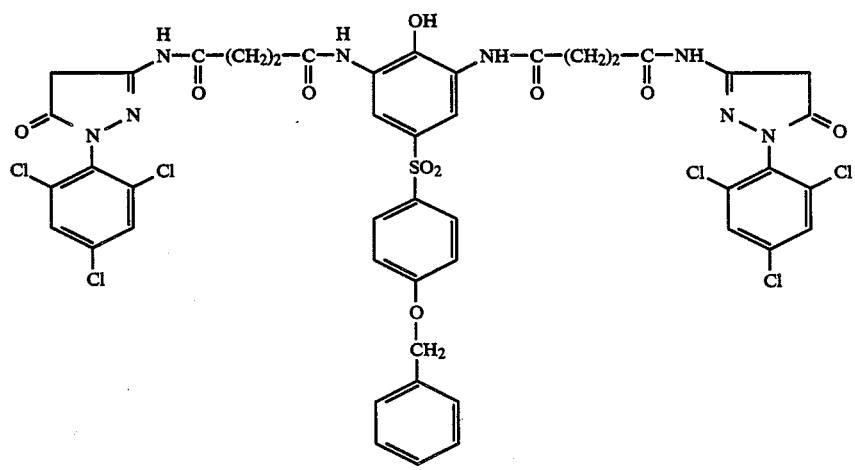
M-7
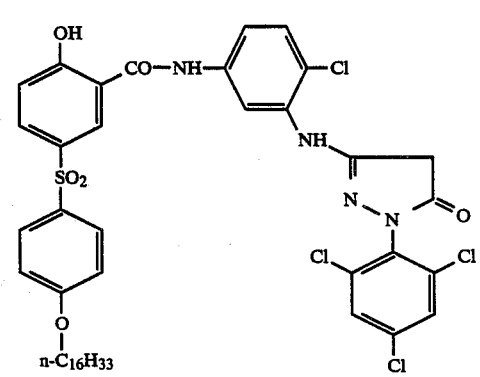

-continued
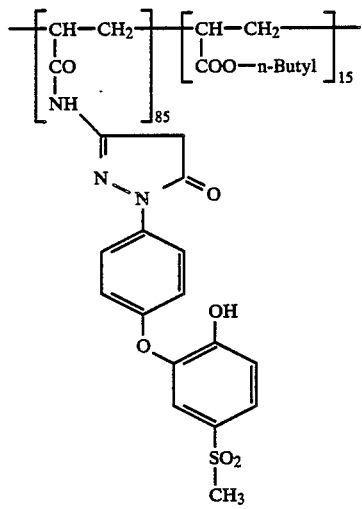
M-8
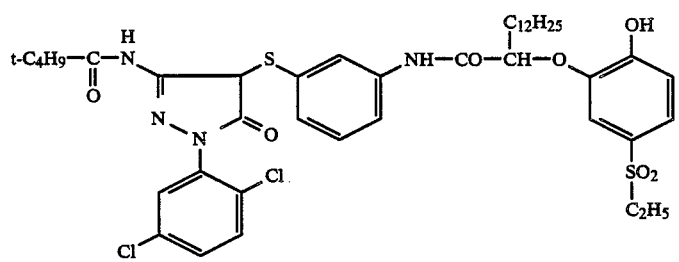
M-9
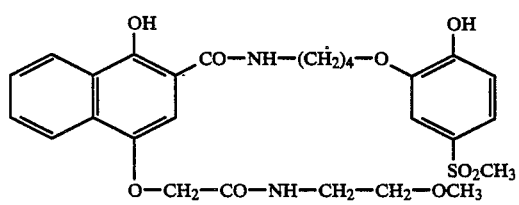
C-1
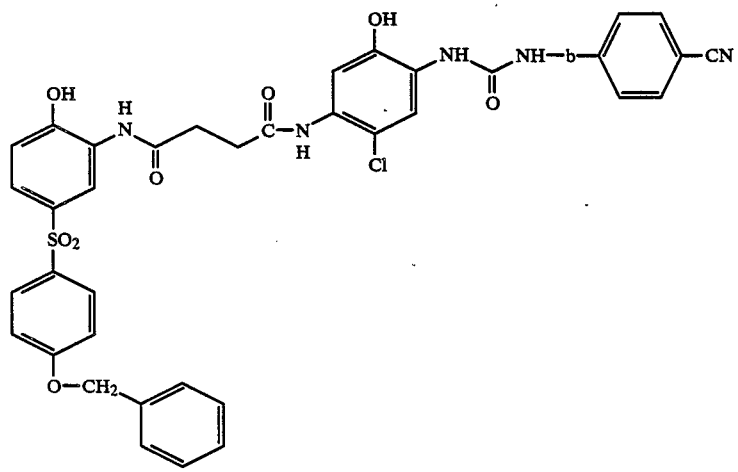
C-2

C-3
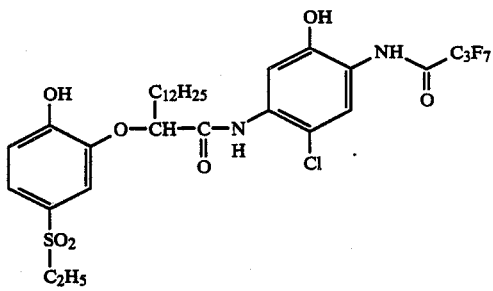
C-4
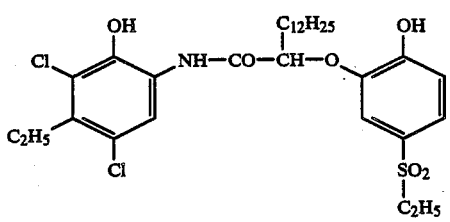
C-5
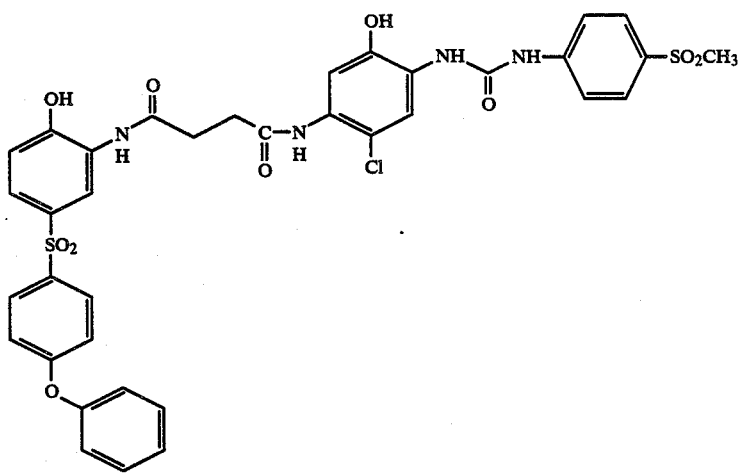
C-6
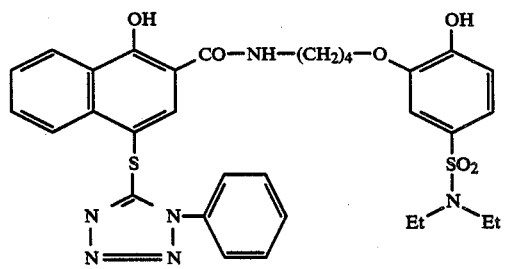
C-7
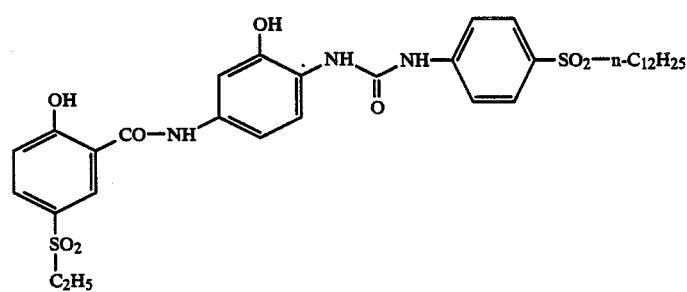

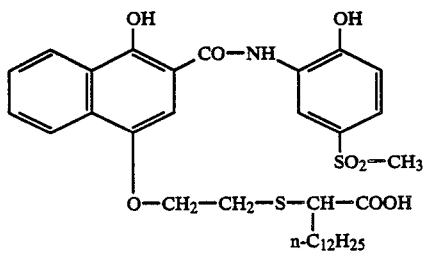

C-8

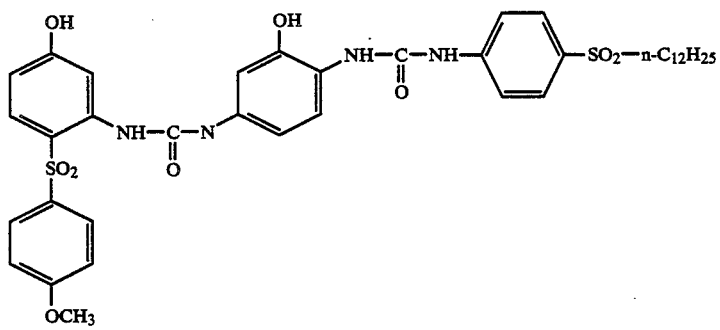

C-9

The synthesis of some of the couplers according to the invention are described below by way of example.

EXAMPLE OF PREPARATION 1

Preparation of coupler M-3

29 g of 7-Chloro-6-methyl-3-[3-(p-aminophenyl)-propyl]-1H-pyrazolo[3,2-c]-s-triazole prepared according to EP-A-0 073 636 were dissolved in 250 ml of i-propanol, and 25 ml of N,N-dimethylaniline were added thereto. 41 g of β-[2-Hydroxy-5-(4-ethoxy-phenylsulphonyl)-anilino-carbonyl]-propionyl chloride dissolved in 50 ml of dioxane were added dropwise in the course of 30 minutes at 10° C. The reaction mixture was then stirred for one hour and poured into 1 l of ice/HCl and the aqueous phase was extracted by shaking with 500 ml of ethyl acetate. After dehydration of sodium sulphate, the solvent was evaporated off at reduced pressure and the residue was separated by column chromatography on silica gel with ethyl acetate/methyl chloride (10:1).

Yield: 50 g Melting point: 163.5° C. with decomposition.

Example of preparation 2

Preparation of coupler C-2

25 ml of N,N-dinethylaniline were aded to 30.3 g of a solution in 250 ml of tetrahydrofuran of 2-(p-cyano-phenylureido)-4-chloro-5-aminophenol prepared according to EP-A 0 028 099. 47.2 g of β-[2-hydroxy-5-(4-benzyloxyphenylsulphonyl)-anilinocarbonyl]-propionyl chloride dissolved in 100 ml of tetrahydrofran were then added dropwise in the course of 30 minutes at 10° C. The reaction mixture was then stirred for one hour at room temperature and precipitated in ice/HCl, and the precipitated product was recrystallised from acetonitrile.

Yield: 45 g Melting point: 174° C.

Example of preparation 3

Preparation of coupler Y-1

40.5 g of α-Pivaloyl-α-(4-carboxy-phenoxy)-2-chloro-5-aminoacetanilide were dissolved in 250 ml of tetrahydrofuran, and 25 ml of N,N-dimethylaniline were added thereto. 31.9 g of β-[2-Hydroxy-5-ethylsul-phonyl-anilinocarbonyl]-propionyl chloride dissolved in 100 ml of tetrahydrofuran were then added dropwise in the course of 30 minutes at 10° C. The reaction mixture was then stirred for one hour at room temperature and introduced into 1 l of ice/HCl, and the oil which separated was suction filtered after solidification. 65 g of coupler Y-1 were obtained after recrystallisation from dioxane/acetone (4:1). M.p. 138°-140° C.

The couplers according to the invention containing a phenyl group substituted with a hydroxyl group and a sulphonyl group have sufficiently hydrophilic properties to enable the dyes to be developed from colour couplers with the required sensitivity and maximum colour density without the aid of special developer additives such as benzyl alcohol which are regarded as intermediaries between the hydrophilic and the hydrophobic phase.

The couplers according to the invention are also particularly distinguished by their excellent solubility and low tendency to crystallisation in organic solvents, in particular in water immiscible solvents with high boiling point such as tricresylphosphate or dibutyl phthalate.

This is found to be advantageous in reducing the weight of substance required in the layer.

In addition, the couplers have excellent resistance to diffusion in photographic layers, both during casting and during photographic processing.

Another advantage of the colour couplers according to the invention is their high stability to moisture and heat as well as the stability of the dyes produced from them to heat, moisture and light.

Lastly, the colour couplers according to the present invention are relatively unaffected by fluctuations in the pH during processing, in particular during development.

The combination of excellent solubility in organic solvents and excellent diffusion resistance on the one hand with high compatibility with water on the other is a particularly unexpected, unforeseeable property of the couplers according to the invention.

In the process of preparing the light-sensitive colour photographic recording material, the diffusion-fast couplers according to the present invention may be incorporated in known manner with the casting solution of the silver halide emulsion layers or other colloid layers. For example, oil-soluble or hydrophobic couplers may advantageously be added to a hydrophilic colloid solution from a solution in a suitable coupler solvent (oil former), optionally in the presence of a wetting agent or dispersing agent. The hydrophilic casting solution may, of course, contain other conventional additives in addition to the binder. The solution of coupler need not be directly dispersed in the casting solution for the silver halide emulsion layer or other water-permeable layer but may advantageously first be dispersed in an aqueous, light-insensitive solution of a hydrophilic colloid and the resulting mixture may then be mixed with the casting solution for the light-sensitive silver halide emulsion layer or other water-permeable layer, optionally after removal of the low boiling organic solvent, before the casting solution is applied.

The light-sensitive silver halide emulsions used may be emulsions of silver chloride, silver bromide or mixtures thereof, optionally with a small silver iodide content of up to 10 mol-%, in one of the conventionally used hydrophilic binders. The binder used for the photographic layers is preferably gelatine although this may be partly or completely replaced by other natural or synthetic binders.

The emulsions may be chemically or spectrally sensitized in the usual manner and the emulsion layers, as also other light-insensitive layers, may be hardened with known hardeners in the usual manner.

Colour photographic recording materials normally contain at least one silver halide emulsion layer for light from each of the three spectral regions, red, green and blue. The light-sensitive layers are spectrally sensitized for this purpose with suitable sensitizing dyes in known manner. Blue-sensitive silver halide emulsion layers need not necessarily contain a spectral sensitizer since the intrinsic sensitivity of the silver halide is in many cases sufficient for recording blue light.

Each of the above-mentioned light-sensitive layers may consist of a single layer or it may be composed of two or more silver halide emulsion partial layers in known manner, e.g. as in the so-called double-layered arrangement (DE-C-1 121 470). Red-sensitive silver halide emulsion layers are normally arranged closer to the layer support than green-sensitive silver halide emulsion layers, which in turn are arranged closer to the support than the blue-sensitive layers, with a light-insensitive yellow filter layer generally arranged between green-sensitive layers and blue-sensitive layers, although other arrangements could conceivably be used. A light-insensitive intermediate layer is generally arranged between layers of differing spectral sensitivities, and this intermediate layer may contain means for preventing faulty diffusion of developer oxidation products. Where several silver halide emulsion layers of the same spectral sensitivity are present, these may be arranged directly adjacent to one another or they may be separated by a light-sensitive layer of a different spectral sensitivity (DE-A-1 958 709, DE-A-2 530 645 and DE-A-2 622 922).

Colour photographic recording materials for the production of multicoloured images normally contain colour producing compounds, in this case in particular colour couplers, in spatial and spectral association with the silver halide emulsion layers of different spectral sensitivity for producing the various partial colour images in cyan, magenta and yellow.

By "spatial association" is meant that the colour coupler is in such a spatial relationship to the silver halide emulsion layer that the coupler and layer are capable of interacting to produce an imagewise correspondence between the silver image resulting from development and the colour image produced from the colour coupler. This generally achieved by providing the colour coupler in the silver halide emulsion layer itself or in a layer of binder adjacent thereto, this layer of binder being optionally insensitive to light.

By "spectral association" is meant that the spectral sensitivity of each of the light-sensitive silver halide emulsion layers and the colour of the partial colour image produced from the spatially associated colour coupler are in a certain relationship to one another such that each of the spectral sensitivities (red, green, blue) has a partial colour image of a different colour associated with it (generally, for example, the colours cyan, magenta and yellow in this sequence).

Each of the differently spectrally sensitized silver halide emulsion layers may have one or more colour couplers associated with it. When several silver halide emulsion layers of the same spectral sensitivity are present, each of them may contain a colour coupler, and these colour couplers need not necessarily be identical, provided only that they give rise at least approximately to the same colour in the process of colour development, this colour being normally one which is complementary to the colour of the light to which the particular silver halide emulsion layers are predominantly sensitive.

In preferred embodiments, therefore, red-sensitive silver halide emulsion layers have at least one non-diffusible colour coupler for producing the cyan partial colour image associated with them, generally a coupler of the phenol or α-naphthol series. Associated with the green-sensitive silver halide emulsion layers is at least one non-diffusible colour coupler for producing the magenta partial colour image, usually a colour coupler of the 5-pyrazolone, indazolone or pyrazolotriazole series. Blue-sensitive silver halide emulsion layers have at least one non-diffusible colour coupler associated with them for producing the yellow partial colour image, generally a colour coupler containing an open-chained ketomethylene group. Colour couplers of this type are known in large numbers and have been described in numerous Patent Specifications. Reference may be made here, for example, to the publications entitled "Farbkuppler" by W. PELZ in "Mitteilungen aus den Forschungslaboratorien der Agfa, Leverkusen/Mu chen", Volume III, page 111 (1961) and by K. VENKATARAMAN in "The Chemistry of Synthetic Dyes", Vol. 4, 341 to 387, Academic Press (1971).

The colour couplers may be conventional 4-equivalent couplers or 2-equivalent couplers which require a smaller quantity of silver halide for producing the colour. 2-Equivalent couplers are derived, as is known, from 4-equivalent couplers by containing, in the coupling position, a substituent which is split off in the coupling reaction. 2-Equivalent couplers include both those which are virtually colourless and those which have an intense self colour which disappears in the process of colour coupling to be replaced by the colour of the image dye produced. The last mentioned couplers may be present in addition in the light-sensitive silver halide emulsion layers to act there as masking couplers to compensate for the unwanted side densities of the image dyes. The 2-equivalent couplers, however, also include the known white couplers which do not produce a dye when they react with colour developer oxidation products. Also to be included among the 2-equivalent couplers are the known DIR couplers. These are couplers in which the coupling position carries a removable group which is released as a diffusible development inhibitor whebn the coupler reacts with colour developer oxidation products. Other photographically active compounds, e.g. development accelerators or fogging agents, may also be released from such couplers as a result of development.

According to this invention, the colour photographic recording material contains at least one coupler, preferably at least one colour coupler, having the structure represented by formula I. The advantages thereby achieved may be seen, for example, from the examples described below. Although the exact relationships are not known in detail, it is assumed that the advantages achieved with the couplers according to the invention are due to the structure of the couplers in formula I, in particular the special structure of the phenyl group substituted with a hydroxyl group and a sulphonyl group.

The characteristic group of the coupler of formula I is not a constituent of the coupler group K. It has no significant influence on the spectral properties of the image dyes produced but acts as so-called emulsifier group which promotes the dispersibility of the coupler and stability of the colour photographic recording material. The colour photographic recording material may therefore contain several different couplers corresponding to formula I, and several or all of the differently spectrally sensitized silver halide emulsion layers, for example, may have such a coupler associated therewith.

In addition to the above-mentioned components, the colour photographic recording material according to the present invention may contain other additives, e.g. antioxidants, dye stabilizing agents and agents for influencing the mechanical and electrostatic properties. For reducing or preventing the disadvantageous effect of UV light on colour images produced with the colour photographic recording material according to the invention, it is advantageous, for example, to use UV absorbent compounds in one or more of the layers contained in the recording material, preferably in one of the upper layers. Suitable UV absorbents are described, for example, in US-A-3 253 921, DE-C-2 036 719 and EP-A-0 057 160.

For producing colour photographic images, the colour photographic recording material according to the invention, which contains at least one silver halide emulsion layer and at least one coupler of formula I associated therewith, is developed with a colour developer compound. The colour developer compound may be any developer compound which in the form of its oxidaton product is capable of reacting with colour couplers to form azomethine dyes. Aromatic compounds of the p-phenylene diamine series containing at least one primary group are suitable colour developer compounds, e.g. N,N-dialkyl-p-phenylene diamines such as N,N-diethyl-p-phenylene diamine, 1-(N-ethyl-N-methyl-sulphonamidoethyl)-3-methyl-p-phenylenediamine, 1-(N-ethyl-N-hydroxyethyl-3-methyl-p-phenylenediamine and 1-(N-ethyl-N-methoxyethyl)-3-methyl-p-phenylenediamine.

EXAMPLE 1

0.03 mol of each of the couplers listed in Table 1 below was dissolved with heating to 60° C. in its own quantity by weight of dibutylphthalate and three times its quantity by weight of ethyl acetate. The solutions were then dispersed in aqueous gelatine with the addition of alkanol B, an alkyl naphthalene sulphonate prepared by DuPont. The dispersions were mixed with a silver chlorobromide emulsion (20 mol-% AgBr) containing 0.1 mol of silver and applied to a polyethylene backed paper support and dried. The photographic materials obtained (Samples 1 to 7) were exposed behind a grey wedge and processed as described below, once with and once without benzyl alcohol (30° C.):

Development 210 s
Bleaching fixing 90 s
Washing 120 s.
The baths had the following composition:
5.0 g 4-amino-3-methyl-N-ethyl-N-($\beta$-methanesulphonamidoethyl)-aniline sulphate
(15.0 ml benzyl alcohol)
2.5 g sodium hexametaphosphate
1.85 g $Na_2SO_3$ sicc.
1.4 g NaBr
0.5 g KBr
39.1 g borax made up with water to 1000 ml; adjusted to pH 10.3 with NaOH. Bleach fixing bath:
50.0 g ethylene diaminotetracetic acid-iron(III)-ammonium complex
50.0 ml $(NH_4)_2SO_3$, 40% solution
140.0 ml $(NH_4)_2SSO_3$, 70% solution
20.0 ml aqueous ammonia, 28%
4.0 g ethylene diaminotetracetic acid made up with water to 1000 ml.

The relative sensitivity and maximum colour density for each of samples 1 to 7 are shown in Table 1. The sensitivity is given in relative values, based on the maximum sensitivity achieved (=100). The values obtained when development is carried out in the presence of benzyl alcohol are given in brackets.

TABLE 1

| Sample | Coupler | rel. sensitivity | $D_{max}$ |
|---|---|---|---|
| 1 | Y-1 | 85 (99) | 2.35 (2.56) |
| 2 | M-3 | 92 (100) | 2.14 (2.82) |
| 3 | M-7 | 90 (97) | 2.32 (2.75) |
| 4 | C-3 | 88 (96) | 2.01 (2.58) |
| 5 | V-1 | 70 (89) | 1.48 (1.99) |
| 6 | V-2 | 55 (92) | 1.50 (2.01) |
| 7 | V-3 | 61 (91) | 1.32 (1.98) |

The following comparison couplers were used:

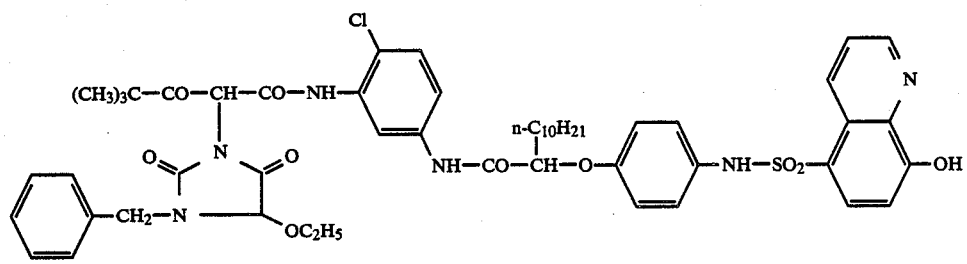

(= Y-7 from US-λ-4 503 141)

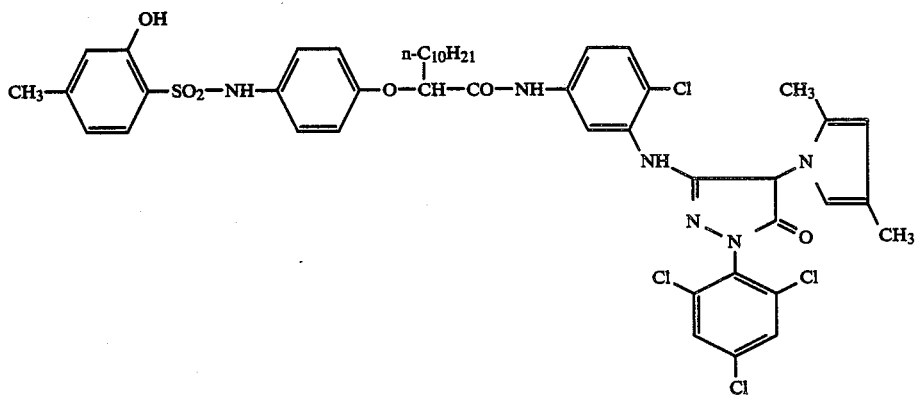

(= M-11 from US-λ-4 513 082)

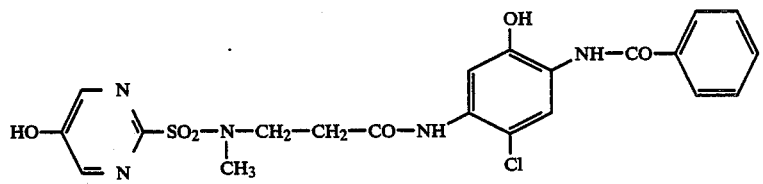

(= C-3 from US-λ-4 503 141)

Table 1 shows that the couplers according to the invention provide a high sensitivity and high colour density even when development is carried out in the absence of benzyl alcohols. They are therefore superior to the comparison couplers.

EXAMPLE 2

Samples 8 to 13 were prepared and processed (development in the presence of benzyl alcohol) in the same manner as described in Example 1. A similar series of experiments was carried out but in which 5 g of sodium dithionite had previously been added to the bleach fixing bath to produce an artificially "exhausted" bleach fixing bath and investigate its effect on the cyan colour density obtained. Table 2 gives the cyan density ($D_{max}$) measured under reflected light when bleach fixing is carried out with a fresh (DA) and an "exhausted" (DB) bleach fixing bath. The percentage residual density given in the last column is determined by the following equation:

$$\text{percentage residual density} = \frac{D_B}{D_A} \times 100$$

TABLE 2

| Sample | Coupler | Colour density $D_{max}$ Fresh / "exhausted" bleach fixing bath | Residual density [%] |
|---|---|---|---|
| 8 | C-5 | 2.35 2.25 | 96 |
| 9 | C-7 | 2.42 2.28 | 94 |
| 10 | C-9 | 2.28 2.20 | 96.5 |
| 11 | V-3 | 2.05 1.84 | 90 |
| 12 | V-4 | 1.98 1.35 | 68 |
| 13 | V-5 | 1.95 1.55 | 79.5 |

From Table 2 it may be seen that the image dyes produced from couplers according to the invention suffer a slight colour loss when treated in exhausted bleach fixing baths. This constitutes an important advantage over the known couplers.

The following comparison couplers were used (V-3 has already been mentioned in Example 1):

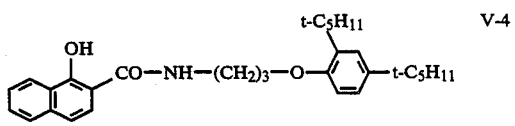

-continued

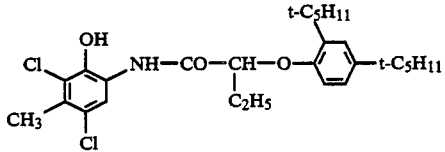 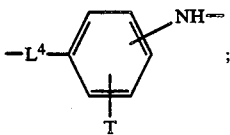  V-5

I claim:
1. Colour photographic recording material having at least one silver halide emulsion layer and at least one coupler containing a phenyl group substituted with a hydroxyl group and a sulphonyl group, characterized in that the coupler corresponds to the following general formula I

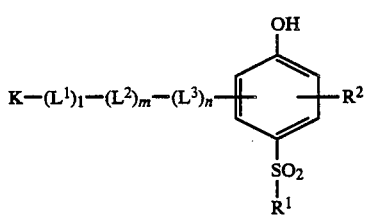

wherein
K represents the residue of a coupler selected from the group consisting of yellow couplers of the type of α-acylacetanilide, magenta couplers of the type of 3-anilino- or 3-acylamino-1-arylpyrazolone and pyrazolotriazole, and naphtholic cyan couplers
$R^1$ represents alkyl, aralkyl, aryl or amino,
$R^2$ represents hydrogen or a group of the formula

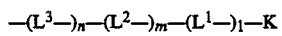

wherein $L^1$ represents —NH— or

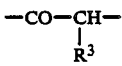 ;

$L^2$ represents —CO—, —CO—CH$_2$—CH$_2$—CO—,

—CO—CH—
       |
       $R^3$ or —$R^4$—;
$L^3$ represents O, NH or —NH—$L^5$—;
$L^4$ represents O, S, NR$^5$, or R$^6$;
$L^5$ represents $R^7$ or a saturated 6-membered carbocyclic ring condensed to the phenyl ring of the group

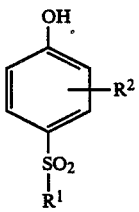

T represents hydrogen, halogen or alkoxy,
$R^3$ and $R^5$ represent hydrogen or alkyl with 1 to 20 carbon atoms,
$R^4$, $R^6$ and $R^7$ represent alkylene with 2 to 4 carbon atoms, and
l, m and n independently of one another have the value 0 or 1.

* * * * *